(12) United States Patent
Yano et al.

(10) Patent No.: US 8,428,883 B2
(45) Date of Patent: Apr. 23, 2013

(54) MULTI-COMPONENT MEDICINE EVALUATION METHOD

(75) Inventors: Kouya Yano, Inashiki-gun (JP); Naoko Hattori, Inashiki-gun (JP)

(73) Assignee: Tsumura & Co., Tokyo (JP)

( * ) Notice: Subject to any disclaimer, the term of this patent is extended or adjusted under 35 U.S.C. 154(b) by 1230 days.

(21) Appl. No.: 11/628,764

(22) PCT Filed: Jun. 6, 2005

(86) PCT No.: PCT/JP2005/010349
§ 371 (c)(1),
(2), (4) Date: Aug. 24, 2007

(87) PCT Pub. No.: WO2005/121777
PCT Pub. Date: Dec. 22, 2005

(65) Prior Publication Data
US 2008/0140375 A1 Jun. 12, 2008

(30) Foreign Application Priority Data
Jun. 7, 2004 (JP) .................................. 2004/008256

(51) Int. Cl.
*G01N 33/48* (2006.01)
*G01N 31/00* (2006.01)
*G06G 7/48* (2006.01)

(52) U.S. Cl.
USPC .................................. 702/19; 702/22; 703/11

(58) Field of Classification Search .......................... None
See application file for complete search history.

(56) References Cited

U.S. PATENT DOCUMENTS
6,906,320 B2 * 6/2005 Sachs et al. .................. 250/282
2002/0138210 A1 9/2002 Wilkes et al.

FOREIGN PATENT DOCUMENTS
| EP | 1 553 515 A1 | 7/2005 |
| JP | 2002 214215 | 7/2002 |
| JP | 2004-187562 | 7/2004 |
| JP | 2005-92466 | 4/2005 |
| WO | WO 02/46739 A1 | 6/2002 |
| WO | WO 2004/111201 A2 | 12/2004 |

OTHER PUBLICATIONS

Naotoshi Shibahara, et al., "A Study of the Quantification of Kampo Medical Questionnaire Data by the MT System", Journal of Quality Engineering Society, vol. 11, No. 5, pp. 78-85, 2003.
Gekkan Yakuji, vol. 28, No. 3, pp. 67-71, 1986.
"Mathematical Principle of Quality Engineering", Japanese Standards Association, pp. 136-141 & 276, 2000.
"Technical Development of Chemistry, Pharmacy and Biology", Japanese Standards Association, pp. 450-457, 1999.
Nilesh K. Shah, et al. "Combination of the Mahalanobis Distance and Residual Variance Pattern Recognition Techniques for Classification of Near-Infrared Reflectance Spectra", Analytical Chemistry, American Chemical Society, vol. 62, No. 5, XP000142072, Mar. 1, 1990, pp. 465-470.

* cited by examiner

*Primary Examiner* — Eric S Dejong
(74) *Attorney, Agent, or Firm* — Oblon, Spivak, McClelland, Maier & Neustadt, L.L.P.

(57) ABSTRACT

A method for evaluation of a multi-component medicine by judging the degree of difference of the multi-component medicine to be evaluated from a group of multi-component medicines selected as a reference group by using a Mahalanobis distance obtained by combining the 3D-HPLC fingerprint data of a multi-component medicine with fingerprint data of 3D-HPLC of other multi-component medicines of the same kind forming a reference group, allocating variable axes in the MT method to the number of multi-component medicine and the elution time or detection wavelength of the fingerprint data, obtaining a unit space from the signal strength, and obtaining the Mahalanobis distance of the multi-component medicine from the unit space.

17 Claims, 5 Drawing Sheets

MULTI-COMPONENT MEDICINE EVALUATION METHOD

TECHNICAL FIELD

The present invention relates to a method for evaluating a multi-component medicine and, more particularly, to a method for evaluating a multi-component medicine, that is, for evaluating the degree of differences of each component forming a multi-component medicine, using a numeric value obtained by applying a specific analytical means to the data measured by three-dimensional high performance liquid chromatography (hereinafter abbreviated from time to time to as "3D-HPLC").

BACKGROUND ART

Quantitative and qualitative profiles of a multi-component medicine, particularly, preparations made from naturally-occurring substances such as a Kampo preparation change according to geological factors, ecological factors, the time, place, and age of collection, weather during growing period, and the like of the raw material herbals to be used. Therefore, a standard for evaluating the qualities, safety, effect, and the like of multi-component medicines such as Kampo preparations is specified, based on which such medicines are evaluated by national regulatory authorities, chemical organizations, manufacturers, and the other organizations concerned.

However, the standard for evaluating the qualities and the like of a multi-component medicine are generally prepared based on the content and the like of one or more appropriately selected components characteristic to the multi-component medicine.

For example, Gekkan Yakuji, vol. 28, No. 3, pp. 67-71 (1986) describes that when an essential component of a multi-component medicine cannot be identified, two or more components, having physical properties undergoing quantitative analysis, which are easily soluble in water, not decomposed in hot water, and chemically unreactive with other components are selected and their content is chemically analyzed to employ the resultant values as a standard of evaluation.

On the other hand, a method of analyzing a multi-component medicine using chromatography to obtain ultraviolet-visible absorption spectroscopy for each elution time (hereafter referred to as "fingerprint data") and preparing a standard based on the component information has been known. For example, JP-A-2002-14215 describes a method of evaluating a multi-component medicine by selecting several peaks among fingerprint data and converting the fingerprint data into a bar-code.

However, since the specific component is quantitatively analyzed based on the concept of "content of a specific component" or "peaks of chromatogram of a specific component" in this method, waveform processing by a computer operation is necessary in order to separate the peaks of a specific component from the peaks of other components on a chromatogram and to determine the peak area and height of the specific component. This has been one of the causes of impairment of the accuracy of the data. That is, since there is no reproducibility in a strict sense in the elution time of a peak, there have been dispersion in the results of the waveform processing of the peaks. The dispersion is particularly remarkable when processing a waveform with small and broad peaks or continuous peaks. The method thus lacks reliability as an evaluation method. Furthermore, a considerable amount of time is required for waveform processing using a computer.

Moreover, since the amount of information (the number of data points) is limited to the number of peaks of a specific component in this method, the amount of information cannot be freely increased or decreased and the data processing time cannot be controlled. There is a case in which an optimal evaluation method cannot be established.

Furthermore, because the contents of two or more specific components are obtained as two or more values according to the above-mentioned method, it is necessary to synthesize and judge those values. It has been impossible to evaluate a multi-component medicine using a single numerical value. Namely, it is impossible to indicate how one multi-component medicine to be evaluated differs from a group of multi-component medicines by using a single numerical value.

Therefore, a method for evaluating a multi-component medicine which is almost free from dispersion of data and highly reliable, requires only a short data processing time, and can evaluate the multi-component medicine using a single numerical value has been desired.

DISCLOSURE OF THE INVENTION

In view of this situation, the present inventors have conducted extensive studies. As a result, the inventors have found a method for evaluating the qualities, safety, effect, and the like of a multi-component medicine by a single numerical value using fingerprint data of 3D-HPLC, processing each item of the fingerprint data by a specific method, and mathematically analyzing the resultant data. This finding has led to the completion of the present invention.

Specifically, the present invention provides a method for evaluation of a multi-component medicine comprising judging the degree of difference of the multi-component medicine to be evaluated from a group of multi-component medicines selected as a reference group by using a Mahalanobis distance obtained by a process comprising the following steps (1) to (5), (1) a step of obtaining fingerprint data of 3D-HPLC of the multi-component medicine to be evaluated, (2) a step of combining the fingerprint data obtained in (1) with fingerprint data of 3D-HPLC of other multi-component medicines of the same kind forming a reference group, (3) a step of allocating variable axes in the MT method to the number of multi-component medicine and the elution time or detection wavelength of the fingerprint data of (2) above and regarding a signal strength as a characteristic amount in the MT method, (4) a step of obtaining a unit space from the characteristic amount of (3) using the MT method, and (5) a step of obtaining the Mahalanobis distance of the multi-component medicine to be evaluated using the MT method from the unit space obtained in (4).

The present invention further provides a method for evaluating a multi-component medicine comprising judging the degree of difference of the multi-component medicine to be evaluated from a group of multi-component medicines selected as a reference group by using a Mahalanobis distance obtained by a process comprising the following steps (1) to (8), (1) a step of obtaining fingerprint data of 3D-HPLC of the multi-component medicine to be evaluated, (2) a step of combining the fingerprint data obtained in (1) with fingerprint data of 3D-HPLC of other multi-component medicines of the same kind forming a reference group, (3) a step of allocating variable axes in the MT method to the number of multi-component medicine and either the elution time or detection wavelength of the fingerprint data of (2) above and regarding a signal strength as a characteristic amount in the MT method, (4) a step of obtaining a unit space from the characteristic amount of (3) using the MT method, (5) a step of obtaining the Mahalanobis distance of all multi-component medicines for each detection wavelength or elution time using the MT method from the unit space obtained in (4), (6) a step of allocating variable axes in the MT method to the number of the multi-component medicine and either the elution time or detection wavelength to which the variable axes are not allocated in the step (3) and regarding the Mahalanobis distance obtained in step (5) as a characteristic amount in the MT method, (7) a step of obtaining a second unit space from the characteristic amount of (6) using the MT method, and (8) a step of obtaining the Mahalanobis distance of the multi-component medicine to be evaluated using the MT method from the second unit space obtained in (7).

The present invention also provides a recording medium in which a program for implementing the above-mentioned evaluation method and/or fingerprint data of the reference group for obtaining a unit space are recorded.

BEST MODE FOR CARRYING OUT THE INVENTION

The present invention relates to a method for evaluating a multi-component medicine by a Mahalanobis distance obtained by mathematical analysis of the fingerprint data using the MT method.

There are two methods for conducting the present invention; one is a method comprising the steps (1) to (5), in which the variable axes are allocated once (hereinafter referred to as "the first method of the invention"), and the other is a method comprising the steps (1) to (8), in which the variable axes are allocated twice (hereinafter referred to as "the second method of the invention").

In order to conduct the first method of the invention, fingerprint data of 3D-HPLC of a multi-component medicine must first be obtained in the step (1).

Here, "multi-component medicine" is defined as a medicine containing two or more effective chemical components and preferably includes, but is not particularly limited to, vegetable extracts, herbal medicines, and Kampo preparations in which the vegetable extracts, herbal medicines, and the like are used. There are also no specific limitations to the form of the medicine. For example, a hot water agent, a Kampo preparation extract granule, a Kampo preparation extract solution, a Kampo preparation tablet, Kampo preparation encapsulated formulation, and the like can be given.

3D-HPLC used in the present invention indicates a spectrum of elution components obtained in each of a number of predetermined elution periods.

A column usually used for high performance liquid chromatography can be used as the column for the 3D-HPLC.

Although not specifically limited, the detection wavelength in the 3D-HPLC is two or more wavelengths selected from an ultraviolet to visible ray absorption region of preferably 150 to 900 nm, particularly preferably 200 to 400 nm, and still more preferably 200 to 300 nm.

Although the signal strength of a spectrum may be either transmittance or absorbance, the absorbance is more preferable.

The fingerprint obtained in the step (1) is a chart showing three-dimensionally the signal strength of spectrum versus the elution time and detection wavelength using the 3D-HPLC as shown in FIG. 1(a), for example. Therefore, the fingerprint data comprises the number (lot number) of a multi-component medicine, elution time, detection wavelength, and signal strength.

The fingerprint data using 3D-HPLC can be obtained using a commercially-available apparatus. As the commercially-available apparatus, the LC-VP system manufactured by Shimadzu Corp. and the like can be given.

The step (2) in the first method of the invention is a step of combining the fingerprint data obtained in (1) with fingerprint data of 3D-HPLC of other multi-component medicines of the same kind forming a reference group.

The fingerprint data of the 3D-HPLC of other multi-component medicines of the same kind forming the reference group can also be obtained in the same manner as that mentioned above. Although there is no specific limitation to the differences of measurement conditions, it is preferable to measure both the multi-component medicine to be evaluated and the other multi-component medicines of the same kind forming the reference group under the same conditions using the same column.

"The other multi-component medicines of the same kind forming the reference group" indicates two or more multi-component medicines which, in the case of Kampo preparations, for example, may include Kampo preparations called by the same name, but having a different component composition due to differences in the time, place, and age of collection, the weather during the vegetation period, and the like, that is, due to differences in the geological factors, ecological factors, climatological factors, and the like.

The reference group is selected from two or more multi-component medicines, but is preferably a group of multi-component medicines produced by the same company. It is also preferable that the reference group be a group of multi-component medicines of which the fingerprint data is available.

When standard geological factors, ecological factors, climatological factors, and the like are known, it is preferable to select the multi-component medicines falling under the scope of such factors as a reference group. For example, the year of collection or the place of collection may be limited. It is also preferable to select multi-component medicines sold by a specific company during a certain period of time. Furthermore, when there is a certain medicinal effect or there are two or more multi-component medicines which are desired to be used as a reference, such medicines are also preferably selected. It is also preferable to select all multi-component medicines sold by two or more companies in the same product name. Moreover, the multi-component medicine to be evaluated itself may be used as a member of the reference group.

Although there are no specific limitations to the number of multi-component medicines forming the reference group, five or more medicines are preferable, with 100 or more being particularly preferable.

The step (3) in the first method of the invention is a step of allocating variable axes in the MT method to the number of multi-component medicine and the elution time or detection wavelength of the fingerprint data to obtain a signal strength which is regarded as a characteristic amount in the MT method.

Here, the MT method of the present invention indicates a calculation technique generally known as the MT method in product quality engineering. For example, methods described in "Hinsitukougaku no suuri" (Mathematical Principle of Quality Engineering) published by the Japanese Standards Association, pp. 136-138 (2000), "Hinsitukougaku no ouyoukouza: Kagaku, yakugaku, seibutsugaku no gijutsu kaihatsu" (Technical Development of Chemistry, Pharmacy, and Biology) of Quality Engineering Application Lecture, edited by the Japanese Standards Association, pp. 454-456 (1999), and "Hinsitukougaku" (Product Quality Engineering) 11(5), pp 78-84 (2003) can be given.

Commercially available program software for the MT method can also be used. As examples of the commercially-available MT method program software, PRAT for Research V1.0 and PRAT for Development V1.0, products of Probe Co.; TM-ANOVA of the Japanese Standards Association; MTS Ver. 2.0 for Excel, MT for Windows of Oken Co.; and the like can be given.

In the first method of the invention, variable axes in the MT method are allocated to the number of multi-component medicine and either one of the elution time and the detection wavelength of the fingerprint data to obtain a signal strength which is regarded as a characteristic amount in the MT method.

Although there are no specific limitations to the allocation of variable axes, it is preferable to allocate the elution time to the item axis (x-axis), the number of the multi-component medicines to the number row axis (y-axis) of the MT method, and a signal strength to the characteristic amount of the MT method.

Here, the item axis (x-axis) and the number row axis (y-axis) are defined as follows. Specifically, in the MT method, the mean value $m_j$ and the standard deviation $\sigma_j$ of a set of data $X_{ij}$ in the following Table 1 are determined. Then, using a formula $x_{ij}=(X_{ij}-m_j)/\sigma_j$, wherein the $x_{ij}$ is a normalized value of $X_{ij}$, a correlation coefficient r of i and j is determined, based on which a unit space and Mahalanobis distance are acquired. In this instance, the mean value $m_j$ and standard deviation $\sigma_j$ are determined by changing the value of the number row axis (y-axis) for each value of the item axis (x-axis).

TABLE 1

| | Item axis (x axis) | | | | |
|---|---|---|---|---|---|
| Number row axis (y axis) | Item 1 | Item 2 | ... | Item j | Item k |
| No. 1 of multi-component medicine | $X_{11}$ | $X_{12}$ | ... | ... | $X_{1k}$ |
| No. 2 of multi-component medicine | $X_{21}$ | $X_{22}$ | ... | ... | $X_{2k}$ |
| No. i of multi-component medicine | ... | ... | ... | $X_{ij}$ | ... |
| No. n of multi-component medicine | $X_{n1}$ | $X_{n2}$ | ... | ... | $X_{nk}$ |

The step (4) in the first method of the invention is a step of obtaining a standard point and unit amount (hereinafter referred to from time to time as "unit space") using the MT method from the data and characteristic amount to which the axes are allocated in the step (3). Here, the standard point, unit amount, and unit space are defined according to the above-mentioned prior art document on the MT method.

The step (5) in the first method of the invention is a step of obtaining a Mahalanobis distance of a multi-component medicine to be evaluated from the unit space (described as "$D^2$" in the MT method) using the MT method. Here, the Mahalanobis distance ($D^2$) is defined according to the above-mentioned prior art document on the MT method and determined using the method described in that prior art document.

When the number and the elution time of multi-component medicines are selected as the variable axes, the Mahalanobis distance of each multi-component medicine can be obtained for each detection wavelength. When the number and the detection wavelength of multi-component medicines are selected as variable axes, the Mahalanobis distance of each multi-component medicine can be obtained for each elution time. When the elution time is allocated to the item axis (x-axis), the number of the multi-component medicines is allocated to the number row axis (y-axis), and a signal strength is allocated to the characteristic amount of the MT method, the Mahalanobis distance ($D^2$) can be obtained for each detection wavelength.

The degree of difference of the multi-component medicine to be evaluated from a group of multi-component medicines selected as a reference group can be appropriately judged by using the Mahalanobis distance obtained in this manner.

The second method of the invention relates to the application of the method commonly called the resolution synthetic method, the multi-MT method, or the multi-stage MT method.

In order to perform the second method of the invention, the steps (1) to (5) are performed in the same manner as in the first method of the invention.

The step (6) of the second method of the invention is a step of allocating variable axes in the MT method to the number of the multi-component medicine and either the elution time or detection wavelength to which the variable axis is not allocated in the step (3), and regarding the Mahalanobis distance to be the characteristic amount in the MT method.

For example, when the elution time is allocated to the item axis (x-axis), the number of the multi-component medicines is allocated to the number row axis (y-axis), and a signal strength is allocated to the characteristic amount of the MT method in the step (3), the Mahalanobis distance for the number of each multi-component medicine can be obtained for each detection wavelength. Following this, a method of allocating the detection wavelength to the item axis (x-axis), the number of the multi-component medicines to the number row axis (y-axis), and the Mahalanobis distance obtained in the above steps (1) to (5) to the characteristic amount of the MT method is preferable.

The step (7) in the second method of the invention is a step of acquiring a second unit space based on a group of data to which an axis was newly allocated in the same manner as in the step (4).

The step (8) in the second method of the invention is a step of obtaining the Mahalanobis distance of the multi-component medicine to be evaluated using the MT method from the second unit space obtained in the step (7).

The degree of difference of the multi-component medicine to be evaluated from a group of multi-component medicines selected as a reference group can be appropriately judged by using the Mahalanobis distance obtained in the step (8) (hereinafter referred to from time to time as "synthetic Mahalanobis distance").

The use of the synthetic Mahalanobis distance is particularly preferable, because the evaluation taking all of the elution time, the detection wavelength, and the number of the multi-component medicines into consideration is possible, whereby the advantage of 3D-HPLC can be efficiently employed.

In a preferred embodiment of the present invention, 3D-HPLC fingerprint data of a reference group consisting of multi-component medicines produced or sold under the same name by a specific company is previously obtained. Then, the Mahalanobis distance from the unit space of a multi-component medicine to be evaluated which is made available by a different company is determined to judge the degree of difference of the multi-component medicine of the different company from the reference group. A method of selecting a certain reference group to previously determine a fixed unit space obtained from that reference group nationwide or internationally is also preferable, because such a method ensures a nationwide or internationally objective and uniform evaluation of multi-component medicines such as Kampo preparations.

It is also preferable to appropriately compress the fingerprint data in the present invention. That is, it is also preferable to arbitrarily decrease the amount of information of the fingerprint data. In the present invention, it is preferable to compress the number of items of data (measuring points) such as signal strength, the number (lot number) of a multi-component medicine, elution time, detection wavelength, and the like. In respect of the elution time, in particular, since the range of the time for an active component to be eluted from a column may be limited occasionally, it is preferable to compress by selecting only the data of the elution time zone. It is also preferable to compress the detection wavelength by selecting data in a limited wavelength zone, since the absorption spectrum of active components may occasionally exist in a limited wavelength zone. In addition to limiting the data selection range, data can also be compressed by sampling an appropriate number of data points at equal intervals from many data points.

It is preferable to limit the elution time data to the data from the start to the end of elution of active components from a column.

Specifically, the elution time data only during elution of an active component from the column is selected or, in the case of a commercially available common 3D-HPLC apparatus in which the data of signal strength and the like are acquired for every elution time of about 0.3 to 1 second, only the data for even intervals of several seconds selected preferably from a range of 3 to 30 seconds, and more preferably from a range of 5 to 20 seconds, are collected.

Furthermore, it is preferable to reduce the number of the data points to $1/4$ to $1/100$ of the usually available number of data points of 3D-PLC fingerprint data. The number of data points from 100 to 1,000 is preferable, with a particularly preferable number of data points being from 200 to 800.

It is preferable that the wavelength zone having a characteristic absorption of an important active component is selected as the detection wavelength. For example, it is preferable to limit the detection wavelength data to the data in a wavelength zone of 200 to 400 nm, and particularly preferably 200 to 300 nm.

In addition, it is preferable to reduce the number of data points to $1/2$ to $1/50$ of the usually available number of data points of 3D-HPLC fingerprint data. The number of data points from 10 to 100 is preferable, with a particularly preferable number of data points being from 20 to 80. Specifically, a method of selecting only data for every fixed wavelength interval selected preferably from a wavelength of 2 to 25 nm, and particularly preferably 5 to 20 nm, from among the data of signal strength and the like for every wavelength of the order of 1 nm acquired by the 3D-HPLC apparatus can be given, for example.

The evaluation method mentioned above can be preferably used for the quality control of multi-component medicines. In this case, a particularly preferred method of quality control is a method of rejecting a multi-component medicine when the Mahalanobis distance from the unit space of that multi-component medicine which is the subject of quality control is greater than a certain value selected from a fixed range. Although the above fixed range varies according to the type of the multi-component medicine, a range preferably from 2 to 1,000, and particularly preferably from 10 to 100, is given, for example.

The evaluation method of multi-component medicines mentioned above can be preferably used for producing multi-component medicines. In this case, it is preferable to produce the multi-component medicines so that the Mahalanobis distance from the unit space may not be greater than a certain value selected from the fixed range. Although the above fixed range varies according to the type of the multi-component medicine, a range preferably from 2 to 1,000, and particularly preferably from 10 to 100, is given, for example.

Specifically, a method of producing a multi-component medicine in which the multi-component medicine is selected as a product only when the Mahalanobis distance from the unit space of the multi-component medicine being evaluated is not greater than a certain value, a method of producing a multi-component medicine in which two or more multi-component medicines or raw materials for such multi-component medicines are mixed so that the Mahalanobis distance from the unit space of the multi-component medicine being evaluated may not be greater than a certain value, and the like can be given.

The evaluation method of the present invention may comprise using a computer for running a program for the evaluation.

Specifically, a program for judging the degree of difference of one multi-component medicine from two or more multi-component medicines in an integrated manner can be preferably used in order to cause a computer to act as at least the following means (A) to (D), (A) a means for storing fingerprint data acquired from 3D-HPLC of two or more multi-component medicines forming a reference group, (B) a means for inputting the fingerprint data acquired from 3D-HPLC of the multi-component medicine being evaluated and combining that data with the fingerprint data stored in (A) above to produce one data group, (C) a means for allocating variable axes in the MT method to the number of multi-component medicines and the elution time or detection wavelength of the group of data of (B) above to obtain the unit space using a signal strength as a characteristic amount in the MT method, and (D) a means for obtaining a Mahalanobis distance from the above unit space of the multi-component medicine to be evaluated using the MT method.

The computer can be utilized also as an information recording medium or as an information transmitting medium in which the program is stored. Here, the information recording medium refers to an information storing means which can be read or written by a general-purpose computer (a semiconductor memory, flexible disk, hard disk, etc.), an optical readout means (CD-ROM, DVD, etc.), and the like. The information transmitting medium refers to a computer network for supplying program information by acting as a signal carrier (LAN, WAN such as internet, wireless network, etc.), a system communication medium (optical fiber, radio channel, etc.), and the like.

In addition to the above-mentioned program, data of the reference group may be recorded in the information recording medium.

Specifically, the information recording medium comprises (I) a program for performing the above-mentioned means (A) and means (B) and (II) the fingerprint data acquired from 3D-HPLC of the two or more multi-component medicines of the same kind forming a reference group.

In addition, a recording medium in which only the fingerprint data of (II) above is recorded for each multi-component medicine, for example, for each Kampo preparation, is also useful for the evaluation.

According to the present invention, because the waveform processing of HPLC peaks is unnecessary, dispersion among data are small, thereby bringing highly reliable results; because the amount of information (the number of data points) is not limited to the number of peaks of a specific component, the amount of information can be freely increased or decreased; in addition, because it is not necessary to judge by combining the value of the content of two or more components, but can be judged using a single numerical value, the degree of difference of the multi-component medicine to be evaluated from a reference group can be correctly, objectively, simply, and unitarily judged.

EXAMPLE

The present invention will be described in more detail by examples and test examples, which should not be construed as limiting the present invention.

Example 1

Step (1) and Step (2)

Measuring samples were prepared from 344 lots of a Kampo preparation, Keishi-bukuryo-gan (extract granules) (hereinafter referred to as "TJ-25") manufactured by TSUMURA & CO. during the period from 1998 through 2003 and another Kampo preparation, Keishi-bukuryo-gan manufactured by an "A Company" according to the following method to obtain 3D-PLC fingerprint data under the following conditions.

<Method for Preparation of Measuring Samples>

3 g of extract granules from each lot was mixed with 100 ml of methanol and the mixture was stirred using a homogenizer for 100 seconds. After allowing to stand for two minutes, extracts were collected from an intermediate position between the surface and the bottom and filtered through a membrane filter with a prefilter to prepare measuring samples.

<Conditions for Obtaining 3D-HPLC Fingerprint Data>

Measuring device: LC-VP system (made by Shimadzu Corp.)

Deployment column: TSK-GEL 80TS (made by a Tosoh Corp.)

Mobile phase: A Solution: 50 mM acetic acid-ammonium acetate buffer solution

B Solution: Acetonitrile

Gradient conditions: Linear gradient

Column temperature: 40° C.

Flow rate: 1.0 ml/min.

Amount of sample: 30 μl

Detector: SPD-M10 Avp (manufactured by Shimadzu Corp.)

Measuring wavelength: 200 to 400 nm

Analysis software: CLASS-VP (manufactured by Shimadzu Corp.)

The resulting 3D-HPLC fingerprint data was compressed as shown in Table 2.

TABLE 2

|  | Obtained data | Data compressing method |
|---|---|---|
| Elution time (range) | 0-80 min | 8-30 min |
| Elution time (data point) | Measured every 0.64 sec | Measured every 12.8 sec |
| Measuring wavelength (range) | 200-400 nm | 200-300 nm |
| Measuring wavelength (data point) | Measured every 1 nm | Measured every 10 nm |
| Signal strength (effective digit) | Fractions of less than 1 μV (μAbs) were rounded down | Fractions of less than 1 mV (mAbs) were rounded down |

The following data points were obtained.

| Number of multi component medicines | 344 |
|---|---|
| Number of detection wavelengths | 11 |
| Number of elution time | 108 |

An example of the fingerprint before and after the data compression is shown in FIG. 1. As a result, the unit space and Mahalanobis distance can now be calculated by the MT method.

Step (3)

Axes in the MT method were allocated to the resulting 3D-HPLC fingerprint data for each detection wavelength as shown in the right column of Table 3.

As "each detection wavelength", the wavelength from 200 to 300 nm was equally divided into 11 for every 10 nm.

TABLE 3

| Obtained fingerprint data Before allocation of axes For each multi-component medicine | | After allocation of axes For each detection wavelength | |
|---|---|---|---|
| Item axis (x axis) | Detection wavelength | Item axis (x axis) | Elution time |
| Number row axis (y axis) | Elution time | Number row axis (y axis) | Number of multi-component medicine |
| Characteristic amount | Signal strength | Characteristic amount | Signal strength |

In this manner, fingerprint data usually acquired was converted into a form suitable for numerical analysis by the MT method.

Step (4)

The unit space, i.e., the standard point and the unit amount were obtained using the MT method as described in "Hinsitukougaku no suuri" (Mathematical Principle of Quality Engineering) pp 136-138 Japanese Standards Association (2000), "Hinsitukougaku no ouyoukouza: Kagaku, yakugaku, seibutsugaku no gijutsu kaihatsu" (Technical Development of Chemistry, Pharmacy, and Biology) of Quality Engineering Application Lecture, edited by the Japanese Standards Association, pp. 454-456 (1999), and "Hinsitukougaku" (Product Quality Engineering) 11(5), pp 78-84 (2003).

"MT for Windows" developed by Ohken Co., Ltd. was used for calculation.

Step (5)

The Mahalanobis distance from the standard point of the Keishi-bukuryo-gan preparation manufactured by the "A Company" obtained in the step (4) above was determined by the MT method according to the above prior art document.

Next, the Mahalanobis distance of each Keishi-bukuryo-gan preparation was calculated in the same manner as that of the above-mentioned steps (1) through (5), except that instead of the Keishi-bukuryo-gan preparation manufactured by the "A Company", twelve multi-component medicine Kampo preparations listed in Table 4 other than the Keishi-bukuryo-gan preparation manufactured by the "A Company" was used as a multi-component medicine to be evaluated in the step (1).

The Mahalanobis distance was obtained for each of the eleven wavelengths which are obtained by equally dividing the wavelength from 200 to 300 nm into 11 for every 10 nm. As an example, the Mahalanobis distance at 230 nm is shown in Table 4.

TABLE 4

| Keishi-bukuryo-gan | Mahalanobis distance |
|---|---|
| TJ-25-I (manufactured by TSUMURA & CO.) | 14.9 |
| TJ-25-II (manufactured by TSUMURA & CO.) | 13.1 |
| Product manufactured by A company | 227.0 |
| Product manufactured by B company | 64.0 |
| Product I manufactured by C company | 407.7 |
| Product II manufactured by C company | 653.2 |
| Product III manufactured by C company | 81.3 |
| Product IV manufactured by C company | 113.8 |
| Product V manufactured by C company | 96.7 |
| Product manufactured by D company | 33.7 |
| Product manufactured by E company | 28.0 |
| Product manufactured by F company | 84.0 |
| Product manufactured by G company | 1476.4 |

The degree of difference of the Keishi-bukuryo-gan preparations from the reference group could be judged by using the Mahalanobis distance for each detection wavelength obtained in the step (1) through the step (5), whereby the effectiveness of the evaluation method for quality control was verified.

Example 2

In Example 1, the Mahalanobis distance for the number of each multi-component medicine was obtained for each detection wavelength. In this Example, a synthetic Mahalanobis distance was determined by the multistage MT method in the following manner using the Mahalanobis distance obtained in Example 1 as a characteristic amount in the MT method.

Step (1) through Step (5)

These steps were carried out in the same manner as in Example 1.

Step (6)

Axes in the MT method were allocated as shown in Table 5.

TABLE 5

| Allocation of axes | |
|---|---|
| Item axis (x axis) | Detection wavelength |
| Number row axis (y axis) | Number of multi-component medicine |
| Characteristic amount | Mahalanobis distance obtained in Example 1 |

As a result, a set of data shown in Table 6 was obtained.

TABLE 6

| Number row axis (y axis): Number of multi-component medicine | Item axis (x axis): Detection wavelength | | | | |
|---|---|---|---|---|---|
| | 200 nm | 210 nm | ... j ... | 300 nm |
| 1 | $(D_{1,200})^2$ | $(D_{1,210})^2$ | ... | $(D_{1,j})^2$ | ... $(D_{1,300})^2$ |
| 2 | $(D_{2,200})^2$ | $(D_{2,210})^2$ | ... | $(D_{2,j})^2$ | ... $(D_{2,300})^2$ |
| ... | ... | ... | ... | ... | ... |
| i | $(D_{i,200})^2$ | $(D_{i,210})^2$ | ... | $(D_{i,j})^2$ | ... $(D_{i,300})^2$ |
| ... | ... | ... | ... | ... | ... |
| 344 | $(D_{344,200})^2$ | $(D_{344,210})^2$ | ... | $(D_{344,j})^2$ | ... $(D_{344,300})^2$ |

In Table 6, $(D_{i,j})^2$ represents the Mahalanobis distances obtained in Example 1 of a multi-component medicine of the number i at the detection wavelength j.

Step (7) and Step (8)

The unit space was determined and the synthetic Mahalanobis distance was calculated in the same manner as in Example 1.

FIG. 2 shows a drawing prepared by plotting the synthetic Mahalanobis distance of 344 lots of the Keishi-bukuryo-gan (TJ-25) manufactured by TSUMURA & CO. used in common for obtaining the unit space along the horizontal axis and the number of the samples having the corresponding Mahalanobis distance along the vertical axis. Note that, based on the definition, the mean value of the Mahalanobis distance of 344 lots of TJ-25 used in order to obtain the unit space is always 1.

The synthetic Mahalanobis distances from the standard point of two Keishi-bukuryo-gan preparations manufactured by TSUMURA & CO. and eleven Keishi-bukuryo-gan preparations manufactured by other companies, all being the subject of evaluation, are shown in Table 7.

TABLE 7

| Keishi-bukuryo-gan | Synthetic Mahalanobis distance |
|---|---|
| TJ-25-I (manufactured by TSUMURA & CO.) | 63.3 |
| TJ-25-II (manufactured by TSUMURA & CO.) | 222.2 |
| Product manufactured by A company | 2397.6 |
| Product manufactured by B company | 1110.0 |
| Product I manufactured by C company | 4911.5 |
| Product II manufactured by C company | 7496.4 |
| Product III manufactured by C company | 3226.2 |
| Product IV manufactured by C company | 5546.2 |
| Product V manufactured by C company | 3489.5 |
| Product manufactured by D company | 238.6 |
| Product manufactured by E company | 462.8 |
| Product manufactured by F company | 890.7 |
| Product manufactured by G company | 50698.5 |

The degree of difference from 344 Keishi-bukuryo-gan (TJ-25) preparations manufactured by TSUMURA & CO. was judged by using a single numerical value by using the resulting synthetic Mahalanobis distance. In addition, the fact that the preparation produced by "G Company" and the preparation II produced by "C Company", for example, are most different from the reference group of the 344 TJ-25 preparations, and other facts have been revealed.

Moreover, the use of the synthetic Mahalanobis distance ensured a comprehensive evaluation in a wide detection wavelength range.

Furthermore, it was found that Keishi-bukuryo-gan preparations with a constant product quality can be produced by using this evaluation method.

In addition, the recording medium in which the unit space data of the MT method of the Keishi-bukuryo-gan (TJ-25) preparations manufactured by TSUMURA & CO. is recorded was found to be useful for evaluation.

Example 3

Measuring samples were prepared from 100 lots of a Kampo preparation, Hochu-ekki-to (hereinafter referred to as "TJ-41") manufactured by TSUMURA & CO. during the period from 1998 through 2003, in the same manner as in Examples 1 and 2. Then, the 3D-HPLC fingerprint data was obtained under the same conditions as in Examples 1 and 2 to acquire the unit space, i.e. the standard point and unit amount, using the MT method.

The Mahalanobis distances from the unit space of all TJ-41 preparations used for acquiring the above unit space and other six Hochu-ekki-to preparations manufactured by other companies were determined. It was confirmed that the degree of difference of Hochu-ekki-to preparations from the standard point can be easily, correctly, and objectively judged by using the Mahalanobis distance.

A fingerprint of a Hochu-ekki-to (TJ-41) preparation of which the Mahalanobis distance is 1.0 is shown in FIG. 3(a). A fingerprint of a Hochu-ekki-to preparation of which the Mahalanobis distance is 2704 is shown in FIG. 3(b). Although the degree of difference was not clear by observation only of fingerprints, the numerical values of the Mahalanobis distance obtained according to the present invention greatly differ (i.e. 1.0 versus 2704), confirming the effectiveness of the Mahalanobis distance for quantitatively judging the difference of multi-component medicines.

Example 4

Step (1) and Step (2)

Measuring samples were prepared from 251 lots of a Kampo preparation, Tokaku-joki-to (extract granules) (hereinafter referred to as "TJ-61") manufactured by TSUMURA & CO. during the period from 1999 through 2003, and another Kampo preparation, Tokaku-joki-to manufactured by A Company, according to the following method to obtain 3D-HPLC fingerprint data under the following conditions.

<Method for Preparation of Measuring Samples>

2 g of extract granules from each lot were mixed with 100 ml of methanol and the mixture was stirred using a homogenizer for 100 seconds. After allowing to stand for two minutes, extracts were collected from an intermediate position between the surface and the bottom and filtered through a membrane filter with a prefilter to prepare measuring samples.

<Conditions for Obtaining 3D-HPLC Fingerprint Data>

Measuring device: LC-VP system (made by Shimadzu Corp.)
Deployment column: TSK-GEL 80TS (made by a Tosoh-Corp.)
Mobile phase: A Solution: 50 mM acetic acid-ammonium acetate buffer solution
B Solution: Acetonitrile
Gradient conditions: Linear gradient
Column temperature: 40° C.
Flow rate: 1.0 ml/min.
Amount of sample: 30 μl
Detector: SPD-M10 Avp (manufactured by Shimadzu Corp.)
Measuring wavelength: 200 to 400 nm
Analysis software: CLASS-VP (manufactured by Shimadzu Corp.)

The resulting 3D-HPLC fingerprint data was compressed as shown in Table 8.

TABLE 8

| | Obtained data | Data compressing method |
|---|---|---|
| Elution time (range) | 0-80 min | 5.12-35.84 min |
| Elution time (data point) | Measured every 0.64 sec | Measured every 12.8 sec |
| Measuring wavelength (range) | 200-400 nm | 200-400 nm |
| Measuring wavelength (data point) | Measured every 1 nm | Measured every 10 nm |
| Signal strength (effective digit) | Fractions of 1 less than μV (μAbs) were rounded down | Fractions of less than 1 mV (mAbs) were rounded down |

The following data points were obtained.

| Number of multi component medicines | 251 |
|---|---|
| Number of detection wavelengths | 21 |
| Number of elution time | 145 |

Step (3)

Axes in the MT method were allocated to the resulting 3D-HPLC fingerprint data for each detection wavelength as shown in the right column of Table 9.

As "each detection wavelength", the wavelength from 200 to 400 nm was equally divided into 21 for every 10 nm.

TABLE 9

| Obtained fingerprint data Before allocation of axes For each multi-component medicine | | After allocation of axes For each detection wavelength | |
|---|---|---|---|
| Item axis (x axis) | Detection wavelength | Item axis (x axis) | Elution time |
| Number row axis (y axis) | Elution time | Number row axis (y axis) | Number of multi-component medicine |
| Characteristic amount | Signal strength | Characteristic amount | Signal strength |

In this manner, fingerprint data usually acquired was converted into a form suitable for numerical analysis by the MT method.

Step (4)

A unit space, i.e., standard point and unit amount were obtained using the MT method.

"MT for Windows" developed by Ohken Co., Ltd. was used for calculation.

Step (5)

The Mahalanobis distance from the standard point of the Tokaku-joki-to preparation manufactured by the A Company obtained at the step (4) above was determined by the MT method.

Next, the Mahalanobis distance of each Tokaku-joki-to preparations was calculated in the same manner as that of the above-mentioned steps (1) through (5), except that instead of the Tokaku-joki-to preparation manufactured by the "A Company", nine multi-component medicine listed in Table 10 other than the Tokaku-joki-to preparation manufactured by the A Company was used as a multi-component medicine to be evaluated in the step (1).

The Mahalanobis distance was obtained for each of the 21 wavelengths which are obtained by equally dividing the wavelength from 200 to 400 into 21 for every 10 nm. As an example, the Mahalanobis distance at 280 nm is shown in Table 10.

TABLE 10

| Keishi-bukuryo-gan | Mahalanobis distance |
|---|---|
| TJ-61-I (manufactured by TSUMURA & CO.) | 21 |
| TJ-61-II (manufactured by TSUMURA & CO.) | 15 |
| TJ-61-III (manufactured by TSUMURA & CO.) | 17 |
| Product manufactured by A company | 101 |
| Product manufactured by B company | 128 |
| Product manufactured by C company | 135 |
| Product manufactured by D company | 869 |
| Product manufactured by E company | 292 |
| Product I manufactured by F company | 2109 |
| Product II manufactured by F company | 884 |

The degree of difference of the Tokaku-joki-to preparations from the reference group could be judged by using the Mahalanobis distance for each detection wavelength obtained in the step (1) through the step (5), whereby the effectiveness of the evaluation method for quality control was verified.

Step (6)

In the steps (1) to (5), the Mahalanobis distance for the number of each multi-component medicine was obtained for each detection wavelength. In these steps, a synthetic Mahalanobis distance was determined by the multistage MT method in the following manner using the Mahalanobis distance obtained in the steps (1) to (5) as a characteristic amount in the MT method.

Axes in the MT method were allocated as shown in Table 11.

TABLE 11

| Allocation of axes | |
|---|---|
| Item axis (x axis) | Detection wavelength |
| Number row axis (y axis) | Number of multi-component medicine |
| Characteristic amount | Mahalanobis distance obtained in step (1) to step (5) |

As a result, a set of data shown in Table 12 was obtained.

TABLE 12

| Number row axis (y axis): Number of multi-component medicine | Item axis (x axis): Detection wavelength | | | | |
|---|---|---|---|---|---|
| | 200 nm | 210 nm | ... | j | ... | 400 nm |
| 1 | $(D_{1,200})^2$ | $(D_{1,210})^2$ | ... | $(D_{1,j})^2$ | ... | $(D_{1,400})^2$ |
| 2 | $(D_{2,200})^2$ | $(D_{2,210})^2$ | ... | $(D_{2,j})^2$ | ... | $(D_{2,400})^2$ |
| ... | ... | ... | ... | ... | ... | ... |
| i | $(D_{i,200})^2$ | $(D_{i,210})^2$ | ... | $(D_{i,j})^2$ | ... | $(D_{i,400})^2$ |
| ... | ... | ... | ... | ... | ... | ... |
| 251 | $(D_{251,200})^2$ | $(D_{251,210})^2$ | ... | $(D_{251,j})^2$ | ... | $(D_{251,400})^2$ |

In Table 12, $(D_{i,j})^2$ represents the Mahalanobis distances obtained in the step (5) of a multi-component medicine of the number i at the detection wavelength j.

Step (7) and Step (8)

The unit space was determined and the synthetic Mahalanobis distance was calculated in the same manner as in the step (1) to step (5).

FIG. 4 shows a drawing prepared by plotting the synthetic Mahalanobis distance of 251 lots of the Tokaku-joki-to (TJ-61) manufactured by TSUMURA & CO. used in common for obtaining the unit space along the horizontal axis and the number of the samples having the corresponding Mahalanobis distance along the vertical axis. Note that, based on the definition, the mean value of the Mahalanobis distance of 251 lots of TJ-61 used in order to obtain the unit space is always 1.

The synthetic Mahalanobis distances from the standard point of three Tokaku-joki-to preparations manufactured by TSUMURA & CO. and seven Tokaku-joki-to preparations manufactured by other companies, all being the subject of evaluation, are shown in Table 13.

TABLE 13

| Tokaku-joki-to | Synthetic Mahalanobis distance |
|---|---|
| TJ-61-I (manufactured by TSUMURA & CO.) | 3431 |
| TJ-61-II (manufactured by TSUMURA & CO.) | 3190 |
| TJ-61-III (manufactured by TSUMURA & CO.) | 3421 |
| Product manufactured by A company | 112335 |
| Product manufactured by B company | 475053 |
| Product manufactured by C company | 65832 |
| Product manufactured by D company | 11944073 |
| Product manufactured by E company | 8304332 |
| Product I manufactured by F company | 35178330 |
| Product II manufactured by F company | 2783134 |

The degree of difference from 251 Tokaku-joki-to (TJ-61) preparations manufactured by TSUMURA & CO. was judged by using a single numerical value by using the resulting synthetic Mahalanobis distance. In addition, the fact that the preparation I produced by "F Company" and the preparation produced by "D Company", for example, are most different from the reference group of the 252 TJ-61 preparations, and other facts have been revealed.

A fingerprint of Tokaku-joki-to (TJ-61) preparation of which the Mahalanobis distance is 1.0 is shown in FIG. 5(a). A fingerprint of a Tokaku-joki-to preparation of which the Mahalanobis distance is 35178330 is shown in FIG. 5(b).

INDUSTRIAL APPLICABILITY

According to the present invention which is highly reliable and in which the amount of information can be freely increased or decreased, the data processing time can be adequately decreased and the degree of difference of a multi-component medicine to be evaluated from a reference group can be easily judged by using a single numerical value. Since the degree of the difference of a multi-component medicine can be easily evaluated, the method can be used for in-house quality control. Moreover, a multi-component medicine can be suitably manufactured using the method.

Furthermore, if a nationwide or international standard is defined as the unit space of the present invention, the degree of difference of a certain multi-component medicine from the standard thereof can be judged, whereby it is possible to constantly supply multi-component medicines such as Kampo preparations with a stable quality.

Figure 1:
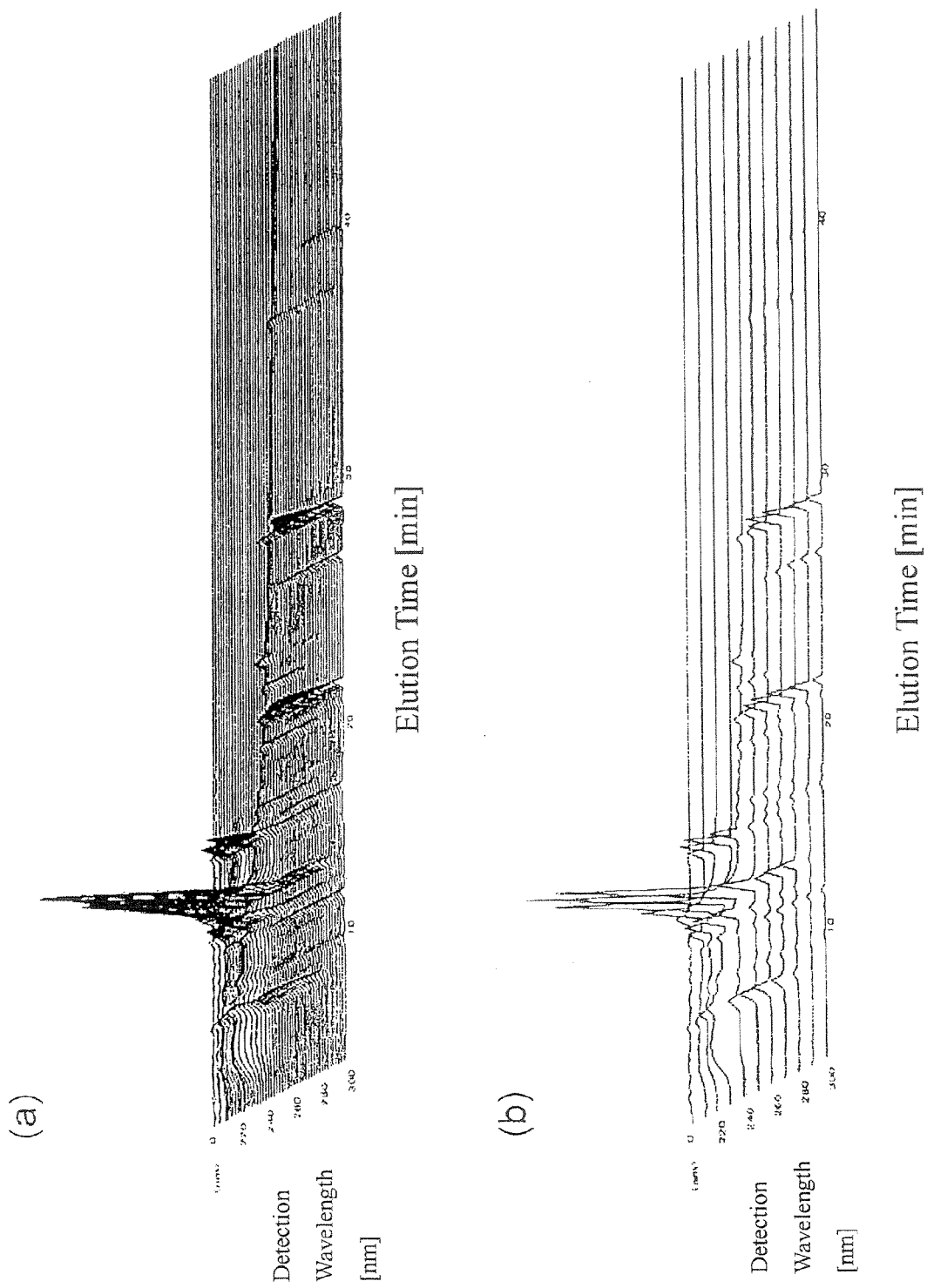
FIG. 1 shows a fingerprint of a Keishi-bukuryo-gan Kampo preparation before and after data compression, wherein (a) is the fingerprint before data compression and (b) is the fingerprint after data compression.
Figure 2:
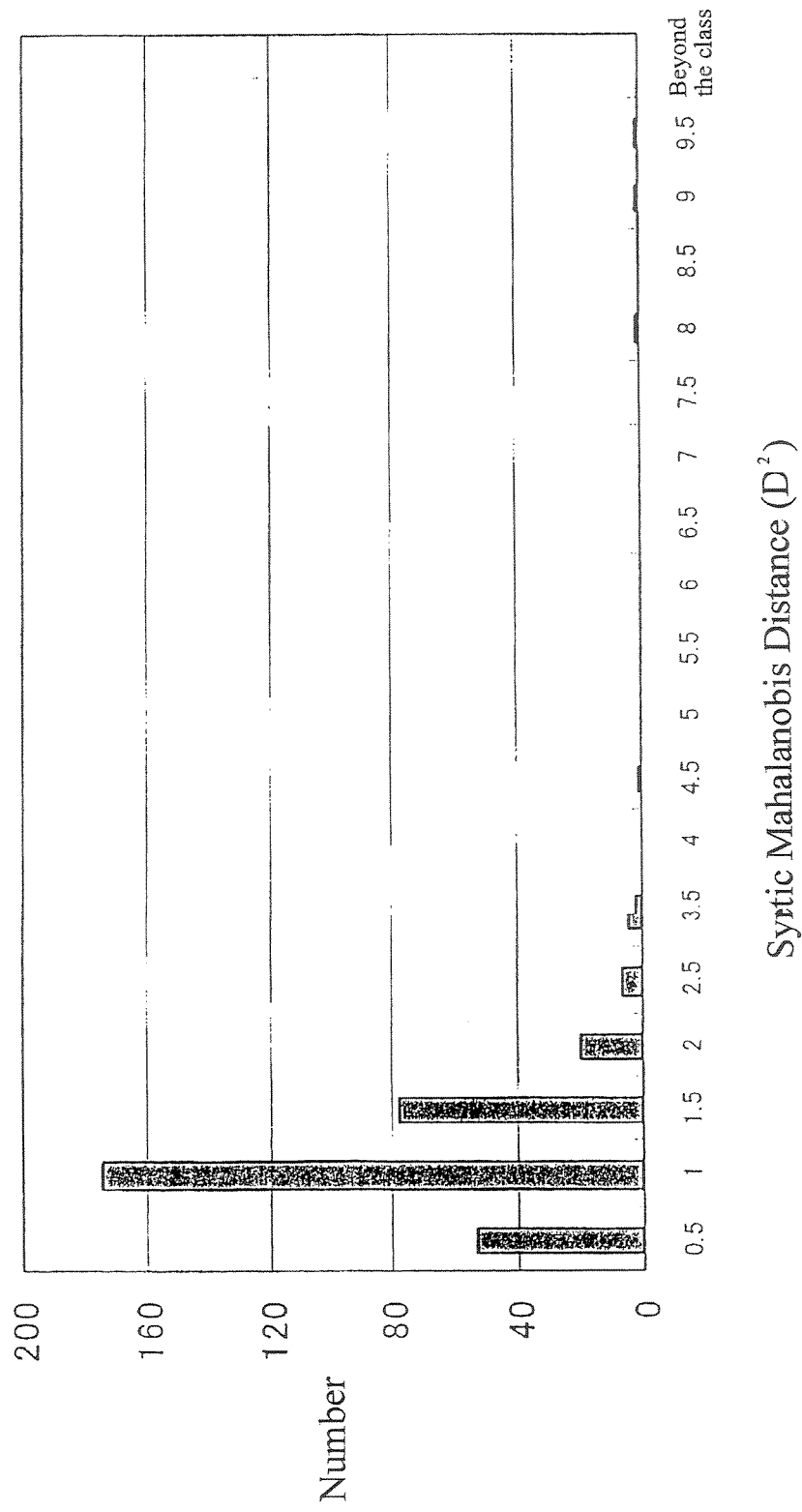
FIG. 2 shows the relationship between the Mahalanobis distance and the number of 344 Keishi-bukuryo-gan Kampo preparations ("TJ-25" manufactured by TSUMURA & CO.).
Figure 3:
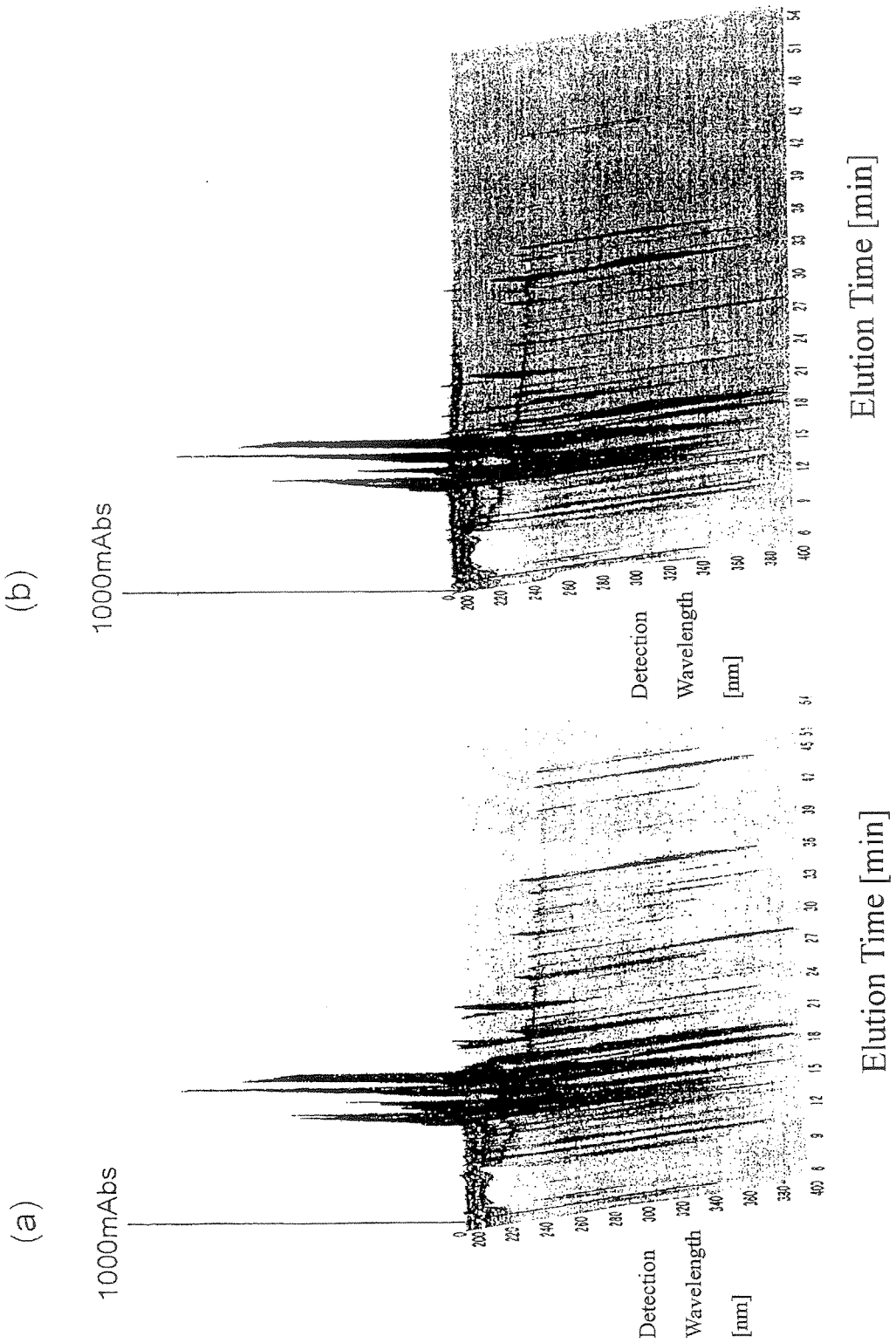
FIG. 3 shows a fingerprint of Hochu-ekki-to preparation ("TJ-41" manufactured by TSUMURA & CO.) with the Mahalanobis distance of 1.0 and the fingerprint of another Hochu-ekki-to preparation with the Mahalanobis distance of 2704, wherein (a) is the fingerprint with the Mahalanobis distance of 1.0 and (b) is the fingerprint with the Mahalanobis distance of 2704.
Figure 4:
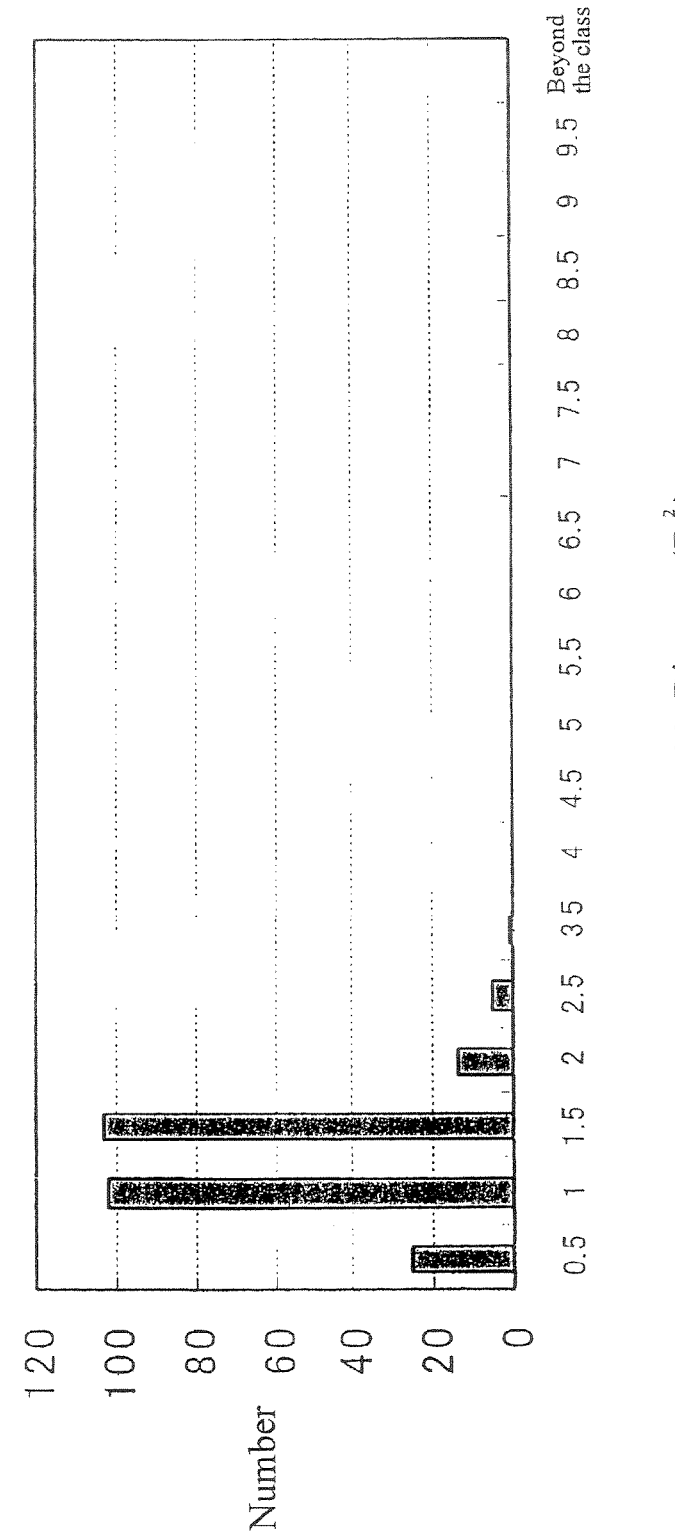
FIG. 4 shows the relationship between the Mahalanobis distance and the number of 251 Tokaku-joki-to Kampo preparations ("TJ-61" manufactured by TSUMURA & CO.).
Figure 5:
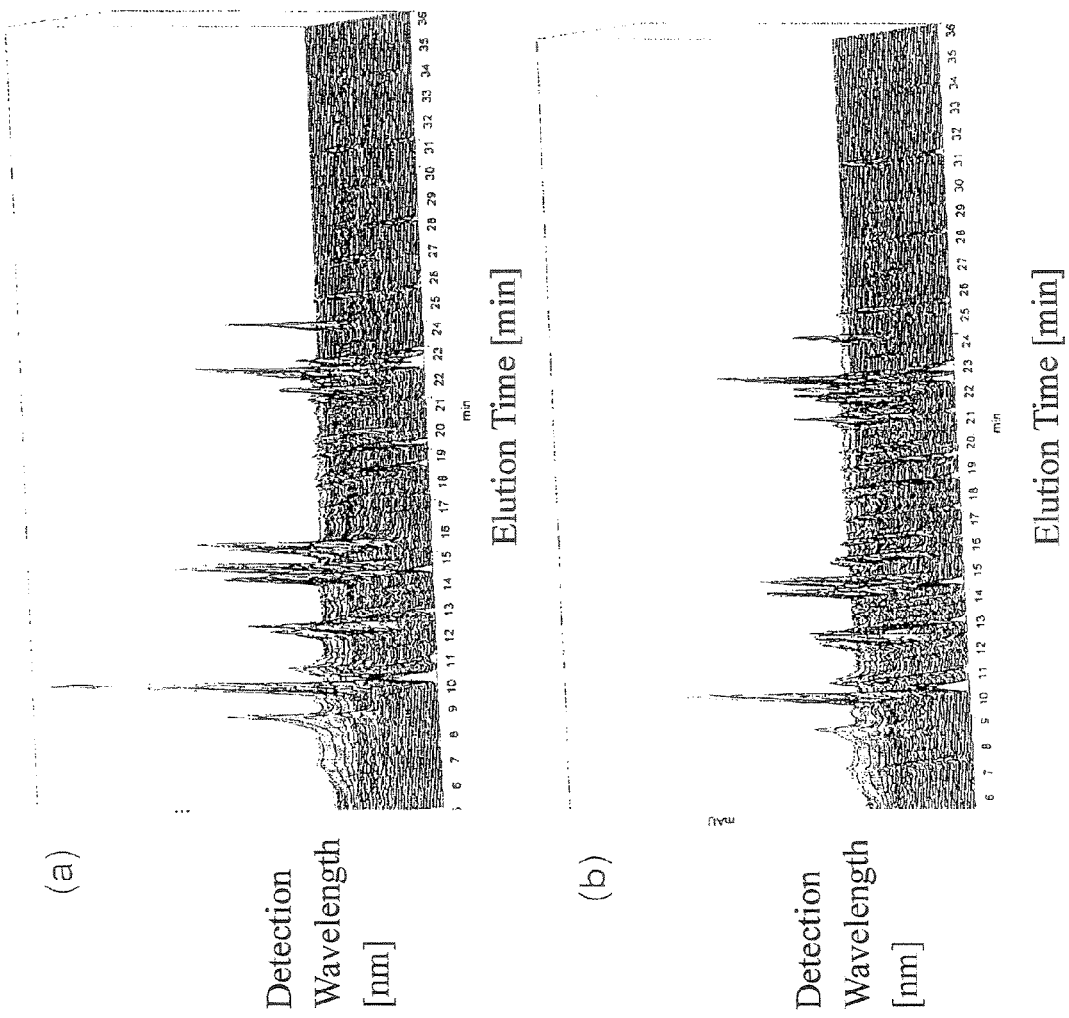
FIG. 5 shows a fingerprint of Tokaku-joki-to preparation ("TJ-61" manufactured by TSUMURA & CO.) with the Mahalanobis distance of 1.0 and the fingerprint of another Tokaku-joki-to preparation with the Mahalanobis distance of 35178330.

The invention claimed is:

1. A computer implemented method for evaluation of a multi-component medicine comprising:
   providing a programmed processor that performs the following:
   (1) obtaining chromatographic high performance liquid chromatography fingerprint data of three-dimensional high performance liquid chromatography of the multi-component medicine to be evaluated,
   (2) combining the chromatographic high performance liquid chromatography fingerprint data obtained in (1) with chromatographic high performance liquid chromatography fingerprint data of three-dimensional high performance liquid chromatography of other multi-component medicines of the same kind forming a chromatographic high performance liquid chromatography fingerprint data reference group,
   (3) allocating variable axes to the number of multi-component medicine and the elution time or detection wavelength of the chromatographic high performance liquid chromatography fingerprint data reference group of (2) above and regarding a signal strength as a characteristic amount,
   (4) obtaining a unit space from the characteristic amount of (3), and
   (5) obtaining the Mahalanobis distance of the multi-component medicine to be evaluated from the unit space obtained in (4).

2. The computer implemented method for evaluation of a multi-component medicine according to claim 1, wherein, in (3), the elution time is allocated to an item axis (x axis) and the number of the multi-component medicine is allocated to an number row axis (y axis) according to the following Table 1, and the signal strength is regarded as a characteristic amount,

TABLE 1

| Number row axis (y axis) | Item axis (x axis) | | | | |
| --- | --- | --- | --- | --- | --- |
| | Item 1 | Item 2 | ... | Item j | Item k |
| No. 1 of multi-component medicine | $X_{11}$ | $X_{12}$ | ... | ... | $X_{1k}$ |
| No. 2 of multi-component medicine | $X_{21}$ | $X_{22}$ | ... | ... | $X_{2k}$ |
| No. i of multi-component medicine | ... | ... | ... | $X_{ij}$ | ... |
| No. n of multi-component medicine | $X_{n1}$ | $X_{n2}$ | ... | ... | $X_{nk}$ | wherein to acquire a unit space and Mahalanobis distance a correlation coefficient r of i and j is determined with a formula $x_{ij}=(X_{ij}-m_j)/\sigma_j$, where $x_{ij}$ is a normalized value of $X_{ij}$, and the mean value $m_j$ and standard deviation $\sigma_j$ are determined by changing the value of the number row axis (y-axis) for each value of the item axis (x-axis).

3. The method for evaluation of a multi-component medicine according to claim 1, wherein, in (2), the reference group is a group of multi-component medicines manufactured by a single company.

4. The method for evaluation of a multi-component medicine according to claim 1, wherein, in (2), the reference group is a group of all multi-component medicines of which chromatographic high performance liquid chromatography fingerprint data are obtained.

5. The method for evaluation of a multi-component medicine according to claim 1, wherein the chromatographic high performance liquid chromatography fingerprint data is compressed.

6. The method for evaluation of a multi-component medicine according to claim 5, wherein the data is compressed by limiting the range of the time to the range of the time for an active component of the multi-component medicine to be eluted from a column and sampling an appropriate number of data points at equal intervals of several seconds selected from a range of 3 to 30 seconds of the elution time.

7. The method for evaluation of a multi-component medicine according to claim 5, wherein the data is compressed by sampling 100 to 1,000 data points as the elution time.

8. The method for evaluation of a multi-component medicine according to claim 5, wherein the data is compressed by limiting the data to the data in detection wavelengths selected from a range of 200 to 300 nm.

9. The method for evaluation of a multi-component medicine according to claim 5, wherein the data is compressed by sampling an appropriate number of data points at equal intervals of several wavelengths selected from a range of 2 to 25 nm of the detection wavelength.

10. The method for evaluation of a multi-component medicine according to claim 5, wherein the data is compressed by sampling 10 to 100 data points as the detection wavelength.

11. The method for evaluation of a multi-component medicine according to claim 1, wherein the multi-component medicine is a Kampo preparation.

12. The method for evaluation of a multi-component medicine according to claim 1, wherein the chromatographic high performance liquid chromatography fingerprint data of the three-dimensional high performance liquid chromatography of the multi-component medicine is not separated to a signal strength of each chemical component of the multi-component medicine.

13. The method for evaluation of a multi-component medicine according to claim 1, comprising judging the degree of difference of the multi-component medicine to be evaluated from the group of multi-component medicines selected as a reference group by using the Mahalanobis distance.

14. A computer implemented method for evaluation of a multi-component medicine comprising judging the degree of difference of the multi-component medicine to be evaluated from a group of multi-component medicines selected as a reference group by using a Mahalanobis distance obtained by a process comprising;
  providing a programmed processor that performs the following:
  (1) obtaining chromatographic high performance liquid chromatography fingerprint data of three-dimensional high performance liquid chromatography of the multi-component medicine to be evaluated,
  (2) combining the chromatographic high performance liquid chromatography fingerprint data obtained in (1) with chromatographic high performance liquid chromatography fingerprint data of three-dimensional high performance liquid chromatography of other multi-component medicines of the same kind forming a reference group,
  (3) allocating variable axes to the number of multi-component medicine and either the elution time or detection wavelength of the chromatographic high performance liquid chromatography fingerprint data of (2) above and regarding a signal strength as a characteristic amount,
  (4) obtaining a unit space from the characteristic amount of (3),
  (5) obtaining the Mahalanobis distance of all multi-component medicines for each detection wavelength or elution time from the unit space obtained in (4),
  (6) allocating variable axes to the number of the multi-component medicine and either the elution time or detection wavelength to which the variable axes are not allocated in (3) and regarding the Mahalanobis distance obtained in (5) as a characteristic amount,
  (7) obtaining a second unit space from the characteristic amount of (6), and
  (8) obtaining the Mahalanobis distance of the multi-component medicine to be evaluated from the second unit space obtained in (7).

15. The method for evaluation of a multi-component medicine according to claim 14, wherein, in (6), the detection wavelengh is allocated to an item axis (x axis), the number of the multi-component medicine is allocated to a number row axis (y axis) according to the following Table 1, and the Mahalanobis distance for each detection wavelength obtained in (5) is regarded as a characteristic amount

TABLE 1

| Number row axis (y axis) | Item axis (x axis) | | | | |
| --- | --- | --- | --- | --- | --- |
| | Item 1 | Item 2 | ... | Item j | Item k |
| No. 1 of multi-component medicine | $X_{11}$ | $X_{12}$ | ... | ... | $X_{1k}$ |
| No. 2 of multi-component medicine | $X_{21}$ | $X_{22}$ | ... | ... | $X_{2k}$ |
| No. i of multi-component medicine | ... | ... | ... | $X_{ij}$ | ... |
| No. n of multi-component medicine | $X_{n1}$ | $X_{n2}$ | ... | ... | $X_{nk}$ | wherein to acquire a unit space and Mahalanobis distance a correlation coefficient r of i and j is determined with a formula $x_{ij}=(X_{ij}-m_j)/\sigma_j$, where $x_{ij}$ is a normalized value of $X_{ij}$, and the mean value $m_j$ and standard deviation $\sigma_j$ are determined by changing the value of the number row axis (y-axis) for each value of the item axis (x-axis).

16. A system for judging the degree of difference of one multi-component medicine from two or more multi-component medicines in an integrated manner, the system performing at least the following (A) to (D),
  (A) storing chromatographic high performance liquid chromatography fingerprint data acquired from three-dimensional high performance liquid chromatography of two or more multi-component medicines forming a reference group,
  (B) inputting the chromatographic high performance liquid chromatography fingerprint data acquired from three-dimensional high performance liquid chromatography of the multi-component medicine being evaluated and combining that data with the chromatographic high performance liquid chromatography fingerprint data stored in (A) above to produce one data group,
  (C) allocating variable axes to the number of multi-component medicines and the elution time or detection wavelength of the group of data of (B) above to obtain the unit space using a signal strength as a characteristic, and
  (D) obtaining a Mahalanobis distance from the above unit space of the multi-component medicine to be evaluated.

17. A computer readable storage media that when executed by a computer program carries out the following:
  (A) storing chromatographic high performance liquid chromatography fingerprint data acquired from three-dimensional high performance liquid chromatography of two or more multi-component medicines forming a reference group,
  (B) inputting the chromatographic high performance liquid chromatography fingerprint data acquired from three-dimensional high performance liquid chromatography of the multi-component medicine being evaluated and combining that data with the chromatographic high performance liquid chromatography fingerprint data stored in (A) above to produce one data group,
  (C) allocating variable axes to the number of multi-component medicines and the elution time or detection wavelength of the group of data of (B) above to obtain the unit space using a signal strength as a characteristic amount, and
  (D) obtaining a Mahalanobis distance from the above unit space of the multi-component medicine to be evaluated.

* * * * *